United States Patent
Kyriakou

(10) Patent No.: US 9,968,319 B2
(45) Date of Patent: May 15, 2018

(54) GENERATING AN AT LEAST THREE-DIMENSIONAL DISPLAY DATA SET

(71) Applicant: Yiannis Kyriakou, Spardorf (DE)

(72) Inventor: Yiannis Kyriakou, Spardorf (DE)

(73) Assignee: Siemens Aktiengesellschaft, München (DE)

( * ) Notice: Subject to any disclaimer, the term of this patent is extended or adjusted under 35 U.S.C. 154(b) by 209 days.

(21) Appl. No.: 14/578,430

(22) Filed: Dec. 20, 2014

(65) Prior Publication Data
US 2015/0173699 A1 Jun. 25, 2015

(30) Foreign Application Priority Data

Dec. 20, 2013 (DE) ........................ 10 2013 226 858

(51) Int. Cl.
*A61B 6/00* (2006.01)
*G06T 7/00* (2017.01)
*G06T 7/593* (2017.01)

(52) U.S. Cl.
CPC .............. *A61B 6/466* (2013.01); *A61B 6/469* (2013.01); *A61B 6/481* (2013.01); *A61B 6/501* (2013.01);
(Continued)

(58) Field of Classification Search
None
See application file for complete search history.

(56) References Cited

U.S. PATENT DOCUMENTS

| | | | | |
|---|---|---|---|---|
| 5,369,678 A | * | 11/1994 | Chiu | A61B 6/542 378/152 |
| 6,377,835 B1 | * | 4/2002 | Schoenberg | A61B 5/055 324/306 |

(Continued)

FOREIGN PATENT DOCUMENTS

| | | |
|---|---|---|
| DE | 102007024450 A1 | 11/2008 |
| DE | 102008064127 A1 | 7/2010 |

OTHER PUBLICATIONS

Waechter et al. "Using flow information to support 3D vessel reconstruction from rotational angiography," Med. Phys. vol. 35, No. 7, Jul. 2008.*

(Continued)

*Primary Examiner* — Matthew Bella
*Assistant Examiner* — Soo Shin
(74) *Attorney, Agent, or Firm* — Lempia Summerfield Katz LLC

(57) ABSTRACT

A method for generating an at least three-dimensional display data set of a time parameter relating to the chronological spreading of a contrast medium introduced into a vessel system is provided. A series of chronologically successive x-ray images of digital subtraction angiography from at least two different projection directions showing the chronological spreading of the contrast medium is used. The method includes determining a three-dimensional position for at least one correspondence point and/or correspondence region defined, in each case, in at least one x-ray image of a projection direction. For each three-dimensional position, a time parameter assigned to the three-dimensional position is determined by evaluation of time-intensity curves assigned to the correspondence points or correspondence regions over the series. The display data set formed from the (Continued)

three-dimensional positions is displayed with the assigned time parameters.

20 Claims, 4 Drawing Sheets

(52) U.S. Cl.
CPC ............ *A61B 6/504* (2013.01); *A61B 6/5235* (2013.01); *G06T 7/0012* (2013.01); *G06T 7/593* (2017.01); *A61B 6/4014* (2013.01); *A61B 6/4441* (2013.01); *A61B 6/507* (2013.01); *G06T 2207/10021* (2013.01); *G06T 2207/10116* (2013.01); *G06T 2207/30101* (2013.01)

(56) References Cited

U.S. PATENT DOCUMENTS

| | | | | |
|---|---|---|---|---|
| 6,501,848 | B1* | 12/2002 | Carroll | G06T 11/006 382/128 |
| 6,532,380 | B1* | 3/2003 | Close | A61B 6/481 382/128 |
| 7,742,629 | B2* | 6/2010 | Zarkh | G06T 7/0067 345/419 |
| 2009/0016587 | A1* | 1/2009 | Strobel | A61B 6/469 382/130 |
| 2011/0235885 | A1* | 9/2011 | Rauch | A61B 6/4441 382/131 |

OTHER PUBLICATIONS

Shpilfoygel et al. "X-ray videodensitometric methods for blood flow and velocity measurement: A critical review of literature," Med. Phys. vol. 27, No. 9, Sep. 2000.*

Mitrovic et al. "Evaluation of 3D-2D Registration Methods for Registration of 3D-DSA and 2D-DSA Cerebral Images," Proc. SPIE 8669, Medical Imaging 2013: Image Processing, 866931 (Mar. 13, 2013).*

Kirbas, "A review of Vessel Extraction Techniques and Algorithms," ACM Computing Surveys, vol. 36, No. 2, Jun. 2004, pp. 81-121.*

German Office Action for German Application No. 10 2013 226 858.0, dated Jul. 17, 2014, with English Translation.

* cited by examiner

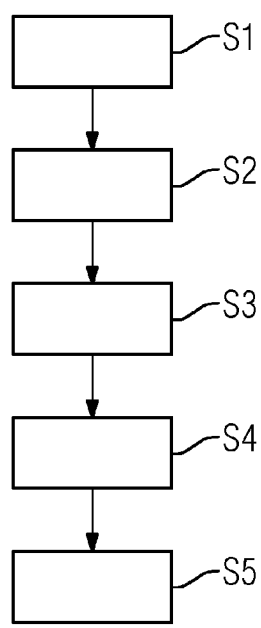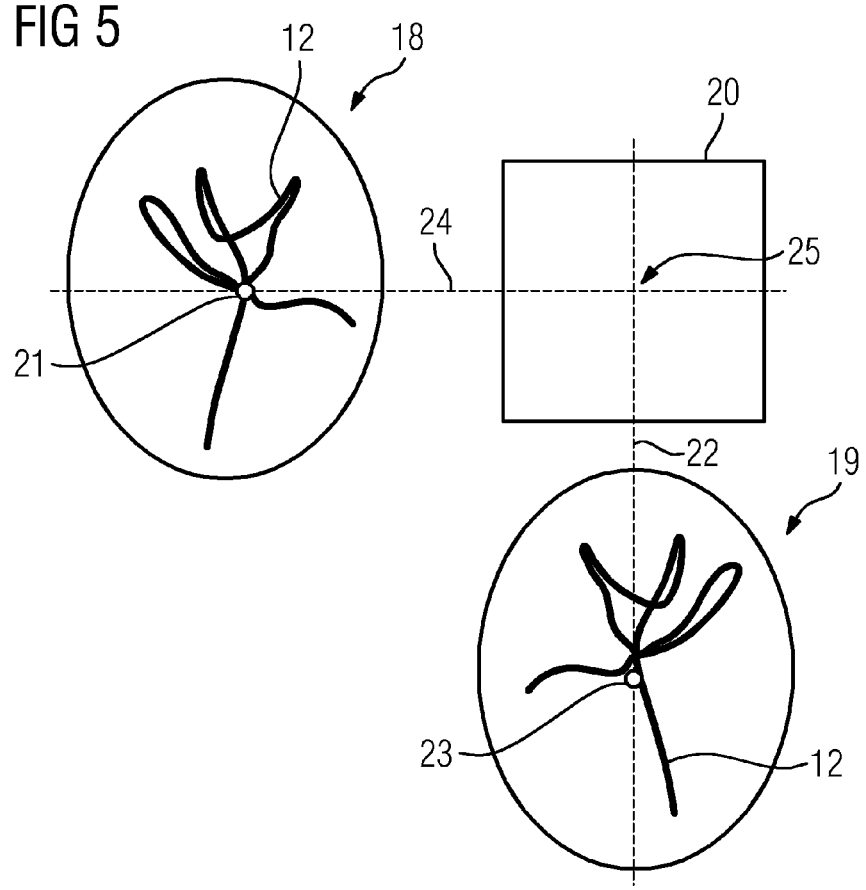

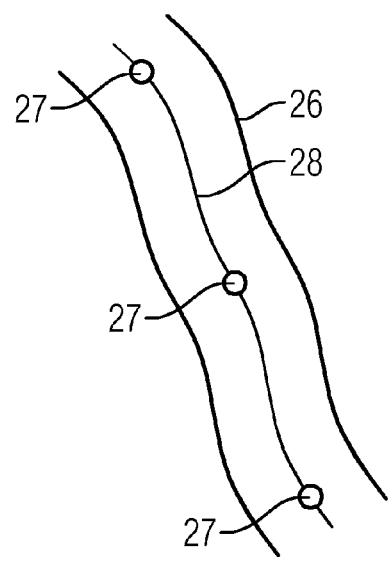
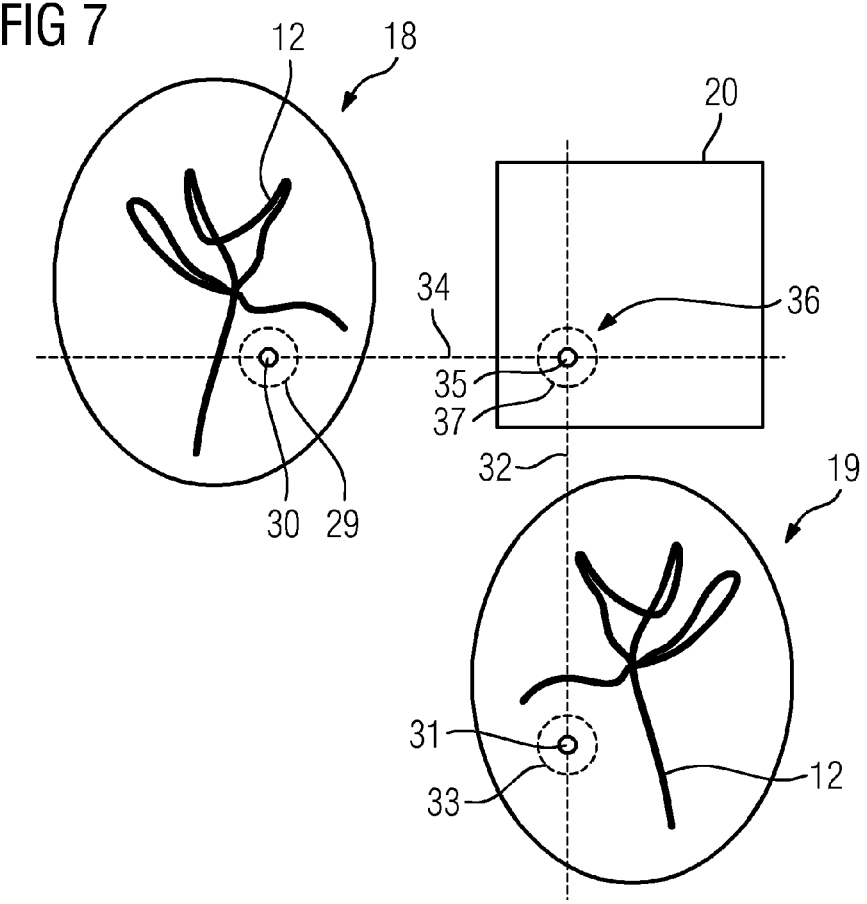

GENERATING AN AT LEAST THREE-DIMENSIONAL DISPLAY DATA SET

This application claims the benefit of DE 10 2013 226 858.0, filed on Dec. 20, 2013, which is hereby incorporated by reference in its entirety.

BACKGROUND

The present embodiments relate to generating an at least three-dimensional display data set of a time parameter relating to chronological spreading of a contrast medium introduced into a vessel system.

It is known in the field of angiography to administer contrast medium that may be clearly recognized in image recordings (e.g., x-ray recordings) and thus permits an assessment of the blood flow and the blood perfusion in the vascular system of a patient and also in the tissue. A classic technique for following the spread of the contrast medium is digital subtraction angiography. In this process, a mask image without contrast medium is recorded. After this, raw images are recorded, often as a chronological series in a time range in which the contrast medium passes through the target region or vascular system of interest, and in which the contrast medium may be seen. In order to remove anatomy that causes interference during evaluation, x-ray images of the digital subtraction angiography are generated in that the mask image is subtracted from the raw image so that essentially only image information relating to the contrast medium remains. In order to obtain better orientation, the two-dimensional digital subtraction angiography may be operated from a plurality of projection directions simultaneously (e.g., by using a biplane system). There may then exist raw images and mask images of the target region, for example, from mutually perpendicular projection directions, so that x-ray images for these mutually perpendicular projection directions are obtained and may be observed and evaluated for diagnosis.

A plurality of time parameters may be determined from two-dimensional subtraction angiography x-ray images, which show the behavior of the contrast medium or are derived therefrom if the time-intensity curves (TIC) are observed in the x-ray images. Herein, for at least some of the image points of interest, the image data (e.g., the intensity) of the x-ray image for all the time points of the series for which an x-ray image exists are plotted against the recording times so that a time-intensity curve is produced (e.g., a contrast medium curve). This is accessible to classic methods of evaluation, and thus, for example, the time to maximum of the contrast medium concentration may be observed at the image point, this usually being known as "time to peak" (TTP). A further, often used time parameter is the mean transit time (MTT), which may be defined in a variety of ways (e.g., relative to the maximum value of the time-intensity curve). The time-intensity curve is also known as TIC.

Importance is also placed on contrast medium-supported examinations in relation to the human brain (e.g., as far as blood perfusion of the parenchyma is concerned). In order to conduct examinations in this regard, regions of interest (ROI) may be defined in the subtraction angiography x-ray images, which are, as far as possible, not overlaid by relatively large vessels. Integration over the time-intensity curve provides information on the quantity of contrast medium that has flowed through at an image point. If the time-intensity curve is observed for a highly interesting region, then this applies for all structures through which x-rays pass. From this, the cerebral blood volume (CBV) and the cerebral blood flow (CBF) may be derived (e.g., in relation to a reference region).

In the prior art, aids that are intended to assist a user in the evaluation of two-dimensional subtraction angiography x-ray images (e.g., for imaging with a biplane x-ray apparatus) have become known. In this regard, time-intensity parameters may be determined from the time-intensity curves for each of the individual x-ray images and, for example, color-coded or displayed using a gray-value scale. Already known, for example, are color-coding systems in which early TTP is assigned a red color, medium TTP is assigned a green color, and high TTP is assigned a blue color. By observing the plurality of projection directions (e.g., two projection directions), the user is able to draw conclusions about where in three-dimensional space interesting vessels/tissues may be found. If it is desired to obtain actual three-dimensional or even four-dimensional information, in place of two-dimensional raw images and assigned mask images, three-dimensional image data sets may be recorded. For example, a rotation of a C-arm about the target region takes place, and reconstruction of three-dimensional image data sets is carried out with the usual reconstruction methods for different time steps during the spreading of the contrast medium. Then, by subtraction of a mask image data set, information about the spreading of the contrast medium may also be included. However, this procedure is extremely time-consuming and also time-critical since the rotations take up a longer period of time, during which a change in the contrast medium situation takes place.

SUMMARY AND DESCRIPTION

The scope of the present invention is defined solely by the appended claims and is not affected to any degree by the statements within this summary.

The present embodiments may obviate one or more of the drawbacks or limitations in the related art. For example, three-dimensional information is made available based also on a series of subtraction angiography x-ray images from a plurality of projection directions.

A method for generating an at least three-dimensional display data set of a time parameter relating to chronological spreading of a contrast medium introduced into a vessel system is provided. A series of chronologically successive x-ray images of digital subtraction angiography from at least two different projection directions showing the chronological spreading of the contrast medium is used. The method includes determining a three-dimensional position for at least one correspondence point and/or correspondence region defined, in each case, in at least one x-ray image of a projection direction. The method also includes, for each three-dimensional position, determining a time parameter assigned to the three-dimensional position by evaluation of time-intensity curves assigned to the correspondence points or correspondence regions over the series, and displaying the display data set formed from the three-dimensional positions with the assigned time parameters.

The basis of the method according to one or more of the present embodiments is therefore the fact that for two mutually corresponding points or regions (e.g., correspondence points/correspondence regions) that are known in x-ray images of different projection directions, a three-dimensional position is derived and may be assigned accordingly. Thus, if, for example, an interesting blood vessel and/or a region of interest (ROI) may be localized, for example, in the parenchyma, in x-ray images assigned to different projection directions, where processing may take place with a biplane system and therefore with two projection directions, then a three-dimensional position may also be assigned. Although significantly too little information is available in order to derive a reliable back-projection and therefore a three-dimensional image data set from the, for example, only two x-ray images, for time parameters derived from the time-intensity curves, a combination of the values derived from the x-ray images of the individual projection directions to a time parameter that may be assigned to the three-dimensional position, which sufficiently accurately reflects the circumstances in order to make useful information available in three dimensions, may be provided. In other words, the method does not provide for back-projecting the x-ray images to a (blurred) three-dimensional image data set, but rather, information derived from the chronological sequence (and thus from many x-ray images) is analyzed in the three-dimensional space. A calculation of time parameters (e.g., dynamic parameters) is therefore used in order to arrive at three-dimensional or, as will be shown in more detail, also at four-dimensional information. Typical examples of such time parameters are a time to the greatest contrast medium concentration (e.g., time to peak (TTP)) and/or a mean transit time (MTT) and/or a relative cerebral blood volume (rCBV) and/or a relative cerebral blood flow (rCBF). The fundamental determination of these time parameters from the time-intensity curves (TIC) is extensively known from the prior art and will therefore not be described in detail here.

Thus, a pseudo-3D or even a pseudo-4D representation of vessel configurations and the like may be easily achieved, so that by the display data set, three-dimensional or even four-dimensional maps with any desired time parameters may be determined. No further x-ray images are necessary, although already existing further three-dimensional image data sets may be included. This is considered in greater detail below. In this way, base information that reflects the information that, in the prior art, is calculated by the user "in his head" and is taken into account without being subject to the abstraction processes that are sometimes barely executable is reconstructed.

If time parameters are available for a plurality of three-dimensional positions, a representation of the display data set may be generated, for example, in that a color code is applied for the time parameters and is used for the corresponding three-dimensional positions. Gray-scales and the like may be used. If, for example, the time parameter is the TTP, red colorations may represent low TTP, yellow and green colorations may represent medium TTP, and blue colorations may represent high TTP. Visualization techniques for at least three-dimensional display data sets are already widely known from the prior art, so that this will not be considered in detail. For example, a rendered representation, a perspective representation or the like may be provided.

Correspondence points or correspondence regions manually determined by a user may be utilized. In most instances, therefore, the correspondence points and/or correspondence regions are to be defined directly or indirectly by a user, where a plurality of aids may be made available for this selection. Thus, in the example of biplane x-ray images, if a correspondence point is known in a projection direction, the associated correspondence point in the other direction is fixed on a particular line (e.g., the epipolar line), which may be drawn in as an aid. The user may obtain maximum benefit from the fact that a whole time series of x-ray images is present. If the user wishes, for example, to mark a correspondence point in the artery, the early x-ray images of the time series may be used because the contrast medium initially flows through the arteries, and therefore, a relatively low TTP is to be expected. A restriction of the selection may accordingly be made in the other projection direction from the chronological standpoint. If, for example, it is already clear from the marking in the first projection direction and/or from an input by the user that an artery is to be marked, the x-ray images of the other projection direction in which the arteries are particularly clearly visible may be made available for selection. A similar time window formation may be provided for veins. In this way, ambiguities that occur when two vessels, through which contrast medium flows at different time points, are overlaid, for example, may be counteracted, so that overall a time-dependent 3D localization that makes it possible for ambiguities to be resolved is produced. Another aid for the user is provided when the x-ray images are segmented before a representation for selecting a correspondence point and/or a correspondence region. Suitable segmentation methods for x-ray images of digital subtraction angiography are known and may therefore also be used in the context of the present invention. All kinds of possibilities may therefore be provided to enable an at least partially automatically supported selection of correspondence points and/or correspondence regions by the user.

In one embodiment, correspondence points and/or correspondence regions (ROIs) may at least partially be determined automatically. For example, for large blood vessels in the human brain, such as the carotid artery, automatic detection methods of this type are already known, so that the center line and therefore points located on the center line may be marked automatically. Such automatic procedures are therefore not excluded in the context of the present embodiments.

An embodiment provides that the correspondence points are determined from a vessel model based on center lines of vessels marked by a user. Therefore, manual marking and modeling of blood vessels may also be undertaken by targeted marking of "center lines". A variety of procedures may be provided (e.g., multiple selection of correspondence points in different projection directions, between which a center line is then determined by automatic fitting and/or interpolation). Another alternative is the complete drawing in of a potential center line by the user, so that thereby, automatic determination of correspondence points that the user may confirm in the other projection direction may be carried out. In this regard, a threshold value-based segmentation of the blood vessels based, for example, on an image of maximum intensity that may be displayed to the user for marking of the center line may be undertaken. With regard to the interpolation of a center line from a plurality of marked correspondence points, and/or to the segmentation, available background knowledge concerning the vessel system may be used (e.g., background information obtained from a three-dimensional image data set such as a CT image data set and/or an MR image data set). The aim of the determination of center lines of the vessels is the at least partial modeling of the vessel system in the recorded target region, although this may be restricted to individual vessels of interest to the user.

The marking of center lines that may determine the position of correspondence points may also be used in an embodiment to determine the vessel model in three-dimensional space from mutually corresponding center lines in at least two projection directions. Through suitable marking of the corresponding center lines, the vessel model may be obtained in three-dimensional space, so that the time-intensity curves may be used along the center lines or for each image point in the two-dimensional x-ray images as input parameters in order to simulate the bolus transit. Differences occurring through overlaying and the like in the individual time-intensity curves of the projection directions have significantly stronger effects than in the consideration of time parameters determined from the whole time series in which, incidentally, background knowledge may also be taken into account, as described in greater detail below. However, if a three-dimensional display data set that is based only on the time-intensity curves is to be generated without assuming any further evaluation, which may be the case in the context of the present embodiments, between individual vessel sections that have no assigned 3D time-intensity curve, the curve may be interpolated from the closest neighbors. Any desired forms of interpolation and combination of the time-intensity curves from the individual two-dimensional data may be used. The accuracy of the vessel model is determined mainly from the number of correspondence points that may be localized in the different projection directions. As mentioned above, however, the method according to one or more of the present embodiments relates centrally to the use of time parameters that, by suitable determination and combination, are better able to compensate for deviations in the time sequence than would be possible with the pure use of time-intensity curves.

A further embodiment provides that by using the vessel model, registration takes place with a three-dimensional image data set of the vessel system. The existence of the vessel model may therefore also be taken into account for a foreseeable registration with a three-dimensional data set, from which a vessel model may also be derived, once the course of vessels is at least partially known.

In addition or alternatively to taking account of a vessel model in the registration with a three-dimensional data set also showing the target region, a registration may take place with a three-dimensional image data set of the vessel system taking account of at least one marker visible in the image data set. In each case, in at least one x-ray image and/or in a raw image underlying the x-ray image of a projection direction and/or gray-scale-based, at least one raw image underlying an x-ray image of a projection direction (e.g., of a mask image) may be taken account of, and/or the registration exists based on the use of an x-ray apparatus for recording the x-ray images and which was also used for the recording of the three-dimensional image data set. Common registration methods may therefore be used, so that three-dimensional positions of the display data set may be placed in relation to a three-dimensional image data set of the vessel system or the target region that may already be recorded, for example, before the recording of the x-ray images. The three-dimensional image data set may be, for example, a CT image data set and/or a magnetic resonance image data set. However, a three-dimensional image data set recorded, for example, with the x-ray apparatus used for the digital subtraction angiography may be used. For immobile patients, this may in any case be registered with the x-ray images. If a marker-based registration is used, anatomical markers may, for example, be used for recordings of the brain, the skull bones and the like. However, for a gray-scale-based registration, for example, an x-ray image of digital subtraction angiography may not be used since the influences of the typical anatomy have been subtracted out of these. Rather, a raw image (e.g., the already always existing mask image) may be used. In this way, a registration of the display data set with an actual three-dimensional image data set is achieved. Actual algorithms for registration are already widely known from the prior art, so that this need not be considered in detail here.

An embodiment provides that the three-dimensional image data set is represented together (e.g., overlaid) with the display data set. In this way, improved orientation of the user in the display data set may be provided.

An embodiment provides that, in order to determine three-dimensional positions, epipolar lines assigned to the correspondence points or correspondence regions are used. Epipolar geometry is well known to persons skilled in the art, where the plane that the projection centers of the recording arrangements for the x-ray images and the recorded object point define is typically called the epipolar plane. The epipolar plane intersects the x-ray images in each case in a straight line that is called the epipolar line. A correspondence point to a correspondence point in another x-ray image may only lie hereon. The epipolar lines therefore form a useful way for determination of the three-dimensional position.

It may also be provided that, in order to determine the three-dimensional position, correspondence points or correspondence regions in a plurality of x-ray image sets recorded at different time points are taken into account. If the totality of the x-ray images recorded at one time point of the series is designated an x-ray image set, the localization in the three-dimensional space may be refined in that correspondence points or correspondence regions in a plurality of x-ray image sets at different time points are taken into account. In this case, use is made of the fact that a plurality of x-ray images in which the correspondence point or the correspondence region may be marked exist, so that by taking account statistically of this plurality of image sources, an improved determination of the three-dimensional position may be provided.

A development provides that for three-dimensional positions assigned to a correspondence region, for determination of the time parameter, the time-intensity curves averaged over the correspondence region are used and/or a single-time parameter of a correspondence region is determined as the mean value of time parameters derived from individual time-intensity curves of the correspondence region. Since a correspondence region may cover a plurality of image points (e.g., pixels) of the x-ray images, and a region is selected for the reason that a statistical observation over this ROI is desired, for example, when observing blood volumes or blood flow in tissues, one embodiment provides for determination, for the correspondence region, of an overall time-intensity curve or at least an overall individual time parameter as the basis for determination of the time parameter assigned to the three-dimensional position by statistical methods (e.g., by averaging). If required, formation of a weighted average is possible, for example, if time-intensity curves strongly deviate at individual image points in the correspondence region and the like.

The time parameter assigned to the three-dimensional position is determined by a combination of individual parameters determined from the time-intensity curves. This provides that the information actually contained in the display data set, the time parameter, at a three-dimensional position is formed by combination of the individual time parameters from the two projection directions, for example. Various possibilities may be provided. It is thus possible for the combination to be made, for example, as a weighted average formation. In this way, a simple linear combination of the individual parameters from the projection directions exists. The use of weightings and possibly other reconstruction methods may enable a further improvement in the determination of the time parameter, where, for example, for the combination of the individual parameters, the time-intensity curves are taken into account. A classic example of this is that it is checked whether an artery or a vein should be observed. For arteries, the time-intensity curve is characterized by a steeper rise and a narrower curve overall, which essentially corresponds to the bolus length. The venous time-intensity curve is more elongated. By comparisons, for example, with curve forms stored in a database, the quality, for example, of the selection of the correspondence point may be assessed, and then, a weighting of both combinations may be determined. Depending on the frame rate, a fit quality for the time-intensity curve may also be used as a weighting in the combination of the individual time parameters. Time window creation and therefore a restriction of the portion of the time-intensity curve that is to be evaluated may also be carried out for at least one projection direction for determination of the time parameter. A process of this type may be provided, for example, if the time-intensity curve for one of the projection directions shows an overlapping of vessels that reach a maximum contrast medium concentration at distinctly different time points (e.g., TTPs). A classic example of such a configuration exists if the projection for one correspondence point that is intended to relate to an artery also records a vein, while the other does not. Then, in order to enable a tidier evaluation of the time-intensity curve, a restriction of the time region under observation may take place such that interfering portions of the vein are kept as slight as possible. Therefore, a time region, in which fewer overlaps are to be found, and only the relevant vessels or regions are observed, is selected. In general terms, therefore, it may be provided that, in order to determine the individual time parameter for at least one projection direction, only one time-limited portion of the time-intensity curve is observed.

For correspondence regions, it may prove to be difficult, under some circumstances, to define an associated correspondence region in other projection directions. For the handling of circular correspondence regions or regions of interest (ROIs), this remains possible due to the inherent symmetry, once the circular correspondence regions or ROIs may be localized based on a simple definition by a center point and a radius as a sphere in three-dimensional space. A more complex case arises if other forms (e.g., ellipses or the like) are to be used. In this regard, a correspondence region may be described by a plurality of circular regions. In the case of non-circular correspondence regions, the correspondence region may be approximated with circles that accordingly may also be found in other projection directions. This provides that the non-circular correspondence region and the corresponding non-spherical three-dimensional volume are approximated as far as possible by circles or spheres. It may thus be provided, for example, that the localization of an ellipse or an ellipsoid in three-dimensional space is carried out by a best-fit approximation of the outline of the respective 2-D ellipse area by a plurality of circles. Thus, the non-circular or, in three-dimensional space, non-spherical ROIs are composed of a plurality of spheres.

A further development provides that, in the case of overlapping three-dimensional positions, for different correspondence regions in the intersecting regions, weighted averaging is carried out for the representation. In one embodiment, correspondence regions that overlap one another are defined as interesting regions in three-dimensional space, described by the three-dimensional position. If a different time parameter is assigned to both the three-dimensional positions, the ROIs assigned to the correspondence regions would be differently represented in three-dimensional space when the display data set is to be displayed. For such cases, therefore, as a type of interpolation in the display data set, in the case of an overlap, for example, a weighted average that may also take account, for example, of what proportion of the overall three-dimensional ROI the intersection region is, is carried out.

A similar problem may also arise in the definition of more complex correspondence regions deviating from the circular form if the correspondence regions are modeled by possibly overlapping circles. If the circles are then initially localized as spheres in three-dimensional space so that as a three-dimensional position, the ROI as an interesting region may be made up in three-dimensional space by the spheres, the circles approximating to the form of the correspondence region may be handled as separate correspondence regions and may be evaluated accordingly. Even for overlapping spheres in three-dimensional space, different time parameters that are to be combined taking account directly of the overlaps may result. For this purpose, a linear combination that takes account in the weighting of the overlap quantity (e.g., the number of three-dimensional voxels overall), the three-dimensional center of gravity, and the like may also be carried out.

As previously mentioned, with the procedure according to one or more of the present embodiments, apart from averaging the time parameters by evaluating the time-intensity curves, a four-dimensional display data set may be generated by defining a time-intensity curve in three-dimensional space for the three-dimensional positions. Its reliability, however, may be relatively low. The method according to one or more of the present embodiments makes it possible, by other ways, to generate at least pseudo-four-dimensional display data sets.

It may thus be provided that at a time point during the series of describing time parameters, a four-dimensional display data set is determined by displaying the time parameter only as the time point is reached. This has been found to be advantageous if, as the time parameter, the time to maximum contrast medium concentration (TTP) is observed. If a representation of the relevant TTP takes place only after the chronological expiry of the TTP, the progress of the contrast medium in the vascular system or target region may also be displayed. The time parameter as a value derived from the entire or at least a large part of the series of x-ray images is to be regarded as more reliable than a point-by-point linking of the time-intensity curves (e.g., if the considerations described are taken into account in the combination of the individual parameters or during their determination). Overall, therefore, even without using the time-intensity curve, the progress of the contrast medium in the target region may be displayed four-dimensionally.

The user may also edit the time parameters in the display data sets manually. If, for example, a time parameter that is clearly implausible to a user is produced, the user may adapt the display data set accordingly by hand so that a meaningful value results there.

In addition to the method, the present embodiments also relate to an x-ray apparatus including a control device for carrying out the method. All embodiments relating to the method may be transferred similarly to the x-ray apparatus, with which the same advantages may therefore be achieved. The x-ray apparatus may be an angiographic system, for example (e.g., a C-arm x-ray apparatus, where the x-ray generator and the x-ray detector are arranged opposite one another on a C-arm). The C-arm x-ray apparatus may be configured as a biplane system, thus having two C-arms that are arranged in a fixed angular position to one another or are freely movable relative to one another. For recording of the x-ray images of the digital subtraction angiography, the recording arrangements are then used in both C-arms so that the projection directions lie perpendicular to one another. In order to be able to control recordings of this type, the control device may have a suitable control unit. The control device may include a DSA unit for the digital subtraction angiography and a three-dimensional position determination unit for determination of three-dimensional positions in the method according to one or more of the present embodiments. The control device may also include a time parameter determining unit for determination of the time parameter, and a display unit that is also configured for displaying the display data set. Further functional units may, for example, include a registration unit for registering with a three-dimensional image data set and the like.

One or more of the present embodiments also relate to a computer program that carries out a method when executed on a computer device. All embodiments relating to the x-ray apparatus and the method may be transferred similarly to the computer program. For example, the computer device may therefore be a control device of an x-ray apparatus. The computer program may be stored on a non-transient data carrier (e.g., a non-transitory computer-readable storage medium such as a CD-ROM).

BRIEF DESCRIPTION OF THE DRAWINGS

FIG. 4 shows a flow diagram of one embodiment of a method;
FIG. 5 shows localization in three-dimensional space;
FIG. 6 shows an exemplary determination of vessel center lines;
FIG. 7 shows an exemplary marking of correspondence regions.

DETAILED DESCRIPTION

The exemplary embodiment of the method described below relates to the creation of a three-dimensional display data set that contains time parameters relating to spread of a contrast medium in a vascular system or derived therefrom. The time parameters are assigned to positions in the three-dimensional space. In the present case, an examination of the head of a patient is considered, where the target of the examination may be either arteries and veins or parenchyma, as will be shown in greater detail below. Where the determination of three-dimensional positions is of interest, in the practical implementation, this corresponds to the marking of particular image elements/voxels of the three-dimensional display data set. This provides that if a three-dimensional position is determined for correspondence points defined in two different projection directions, a voxel is assigned to the correspondence points in the display data set. If a three-dimensional position is determined for correspondence regions, then, where appropriate, depending on the size of the voxel, a plurality of voxels is assigned to the correspondence regions.

The method according to one or more of the present embodiments uses, as a basis, a series of biplane x-ray images of digital subtraction angiography. In this regard (e.g., before administration of the contrast medium in positioned patients), initially two mask images are recorded from the different projection directions with a biplane x-ray apparatus. Following administration of the contrast medium, the recording of a time series of raw images is carried out, showing the spread of the contrast medium in the vascular system (e.g., the vascular system of the brain, as well as the anatomy). In digital subtraction angiography, in order to determine the x-ray images, the mask image made in the same projection direction is subtracted from each raw image of the time series, so that the anatomy portion at least mostly disappears, and only the portions arising from the contrast medium remain, and therefore, the contrast medium-filled vessels are clearly visible.

Figure 1:
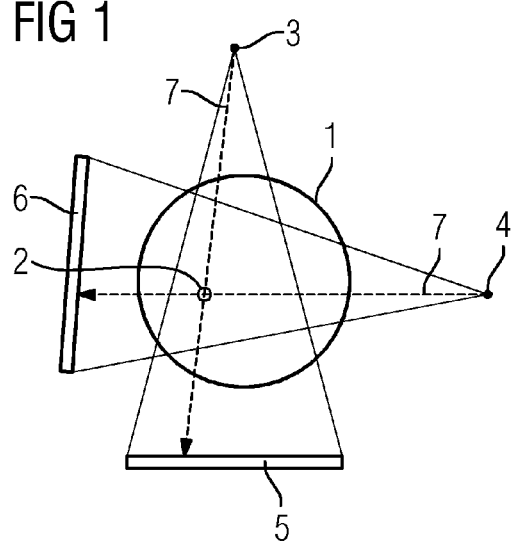
FIG. 1 shows a drawing relating to the biplane recording.

A possible geometry for the recording of such x-ray images is shown in FIG. 1. An object 1 is intended to be imaged. More specifically, the vascular system of interest is provided as the target region, of which a contrast medium-filled vessel 2 is shown emphasized in FIG. 1 by way of example. The biplane x-ray apparatus includes two recording arrangements, each of which has an x-ray generator 3, 4 and an x-ray detector 5, 6, the projection directions of which may be perpendicular to one another for the purpose shown here. As indicated by the arrows 7, the vessel 2 is projected onto different sites of the respective x-ray detector 5, 6 where the vessel 2 therefore also appears in the x-ray image.

Figure 2:
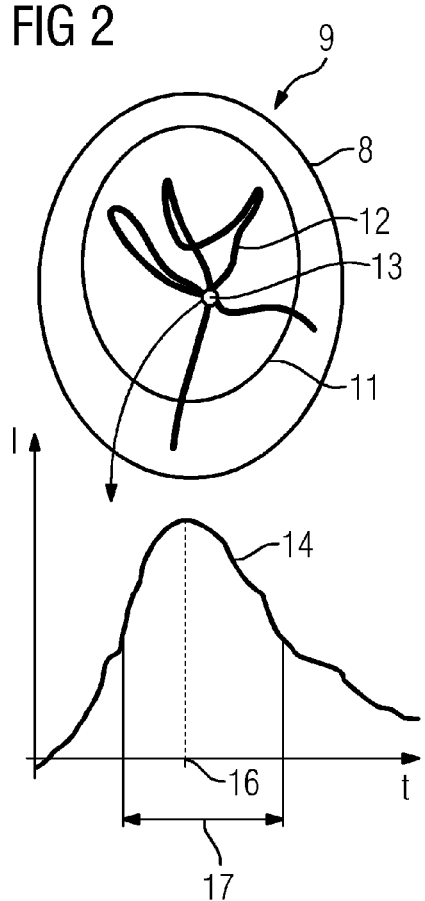
FIG. 2 shows an exemplary x-ray image with an associated time-intensity curve in a first projection direction.
Figure 3:
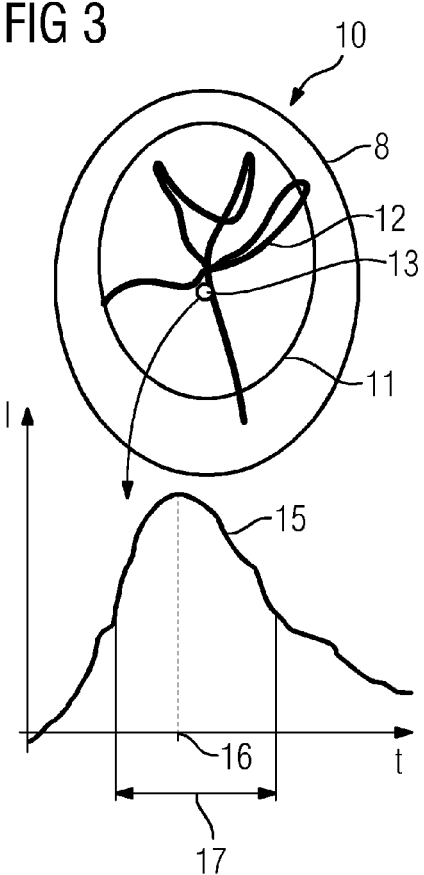
FIG. 3 shows an exemplary x-ray image with an associated time-intensity curve in a second projection direction.

FIGS. 2 and 3 show, as extremely coarse sketches, the basic structure of x-ray images of this type, where the possible outer periphery 8 of the skull of a patient is drawn in merely for orientation purposes. The corresponding signal is no longer contained in the x-ray image 9, 10 due to the performance of digital subtraction angiography. In the x-ray images 9, 10, both the parenchyma 11 in which the contrast medium is distributed, and is therefore present in a lower concentration, and the vascular system indicated at 12 are visible. The correspondence points 13 mark the same vessel in the different x-ray images 9, 10. If a correspondence point 13 of this type is observed or if the intensity measured there is observed over the time series, a time-intensity curve 14, 15 that may be evaluated for the time parameter is produced. Examples of this are the time 16 to the greatest contrast medium concentration (TTP) and the mean transit time 17, which may be defined in various ways using, for example, over half the intensity at TTP 16. For regions in the parenchyma, possibilities are also known for determination of parameters such as the relative cerebral blood volume (rCBV) and the relative cerebral blood flow (rCBF).

Since the time-intensity curves (TICs) 14, 15 each relate to a two-dimensional x-ray image 9, 10, this information is essentially only valid there, and a three-dimensional representation is not useful due to the blurring occurring in a back-projection from only two x-ray images 9, 10.

The method according to one or more of the present embodiments, which is described in greater detail below with reference to FIG. 4, makes an at least three-dimensional display data set that contains information concerning the spreading of the contrast medium or information derived therefrom in the form of time parameters at least for selected points or interesting regions available.

In the present exemplary embodiment, these regions are selected manually in act S1, but also with automatic support.

This is described below with reference to FIG. 5. This again initially shows schematic x-ray images 18, 19 from different projection directions with the at least partially contrast medium-filled vascular system 12. The three-dimensional space is indicated by the box 20. Initially, all the x-ray images of the time series of a projection direction are available to the user, where the user may mark a point of interest (e.g., the correspondence point 21). This may be carried out in an x-ray image 18 in which the vessel is clearly recognizable due to the high contrast medium concentration. In one embodiment, a segmentation of the vessels of the vascular system 12 has already been carried out in the x-ray images in order to assist the user, and an image of the vascular system may be derived from the x-ray images by segmentation and combination of different x-ray images. The selection of the correspondence point 21 in the x-ray image 18 defines as far as a line, the "epipolar line" 22 (e.g., more precisely, where in the x-ray image 19, the other correspondence point 23 lies, so that the epipolar line 22 may also be drawn in on the x-ray image 19 in order to assist the user). Further automated assistance is provided in that the time region of the x-ray images 19 of the other projection direction is restricted about the time point at which the correspondence point 21 was marked, since contrast medium may be in the vessel of interest, in order to be able to mark the vessel of interest.

If, following a selection of this type, the epipolar lines 22 and 24 of the correspondence points 21 and 23 are observed, a three-dimensional position 25, which is also determined automatically in act S2, is produced in the three-dimensional space.

The correspondence points 13 must not necessarily be defined directly as individual points, but may also be given by the center lines of vessels, as the sketch showing the principle in FIG. 6 shows more precisely. Here, a vessel 26 in an x-ray image 9, 10, 18, 19 is shown enlarged with markings 27 placed in the middle by a user. From this, the center line 28 of the vessel 26 may be determined, for example, by interpolation or fitting. Here, also, automatic assistance of the user may take place. In one embodiment, the user draws in the whole center line 28. In this regard, a particularly threshold-based segmentation of the vessels into the x-ray images 9, 10, 18, 19 may be provided since this significantly simplifies the task for the user. Based on the center line 28, interesting correspondence points 13, 21, 23 may be found as soon as the user has found matching center lines 28 in the two projection directions. Also, automatic assistance may take place since for each point of the center line 28, restrictions again arise for the position of the correspondence point for this point in the other projection direction. This may be evaluated through analysis of segmented images, for example, with regard to a pre-selection, which the user then only has to confirm.

FIG. 7 shows that correspondence regions may also be marked in act S1 and, in act S2, may be found in the three-dimensional space. FIG. 7 again shows the x-ray images 18 and 19 and the box 20 indicating the three-dimensional space. Outside the vascular system 12 and therefore in the regions that are as little overlaid with vessels as possible, in the image 18, a correspondence region 29 has been marked that, in the present case, is circular. The correspondence region 29 is thus defined by a midpoint 30 and a radius. Circular correspondence regions 29 of this type may be formed on spheres in three-dimensional space and essentially represent, by a simple definition, the use of correspondence points 13, 21, 23, so that the midpoint 31 in the other projection direction accordingly also lies on an epipolar line 32 that is defined by the midpoint 30. The associated correspondence region 33 may extend around the midpoint 31 with the same radius. If projection into the three-dimensional space takes place using the epipolar lines 32, 34, a sphere 36 is produced there around the midpoint 35 as the three-dimensional position 37. This provides that all voxels of the display data set covered by the sphere 36 are assigned to the correspondence regions 29, 33.

Figure 8:
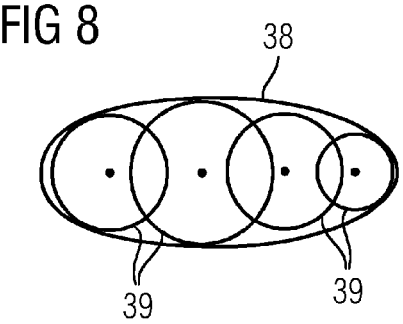
FIG. 8 shows exemplary circles drawn into an ellipse.

FIG. 8 shows how other forms of interesting regions may be configured. Shown in FIG. 8 is an ellipsoid form 38 of a correspondence region in which circles 39 are defined, matching the outer periphery as closely as possible. For these circles 39, corresponding circles in the other projection direction may be found without difficulty, so that an ellipsoid may be approximated in three-dimensional space.

Determination of the respective three-dimensional positions 25, 37 takes place, as previously described, in act S2, based on the epipolar lines 22, 24, 32, 34.

In act S3 (see FIG. 4), time parameters that are assigned to the three-dimensional positions (e.g., to voxels of the display data set) are then determined. In order to determine the assigned time parameters for assigned three-dimensional positions 25 from correspondence points 13, 21, 23, initially individual time parameters are drawn from the time-intensity curves of the respective projection directions at the correspondence points 21, 23, or also taking account of a small surrounding space thereof. As is essentially known, the individual parameters are determined from these time-intensity curves, after which the individual parameters are combined to the time parameter. In the simplest form, this is carried out through averaging, although this may be suitably weighted. The weighting factors are derivable from the image quality, the quality of the time-intensity curve and the like. An embodiment also provides that, for example, where there is overlapping of a plurality of vessels through which contrast medium flows offset in time, only a time-limited portion of the time-intensity curves are evaluated in at least one projection direction. However, quality factors that may be used in the weighting not only relate to such a time limitation of the evaluation, but may also result from an examination of the time-intensity curves. For example, this may be compared with stored reference curves that may relate to typical contrast medium patterns in arteries, veins and/or in tissue. Thus, for example, it is recognized when one of the correspondence points 21, 23 is not optimally selected, and thus, for example, a weaker intensity is present there, and the like.

For correspondence regions, a mean time-intensity curve may be formed over the respective correspondence regions 29, 33. Although, time parameters may be averaged for individual points to the individual time parameter. If the correspondence region 29, 33 is defined by a plurality of circles and/or then spheres, overlaps between the individual circles may be noted when proceeding based on the circles.

In act S4, the three-dimensional positions and the time parameters assigned to the correspondence points 13, 21, 23 and/or correspondence regions 29, 33 are combined, so that a three-dimensional display data set comes about. Therefore, at least part of the voxels that correspond to three-dimensional positions are assigned time parameters determined in act S3. In act S5, the display data set is output on a suitable display device, where the time parameter may be reproduced, for example, color-coded or encoded on a gray-scale. Thus, a user obtains information in three-dimensional space.

The representation of the display data set may be shown overlaid with a three-dimensional data set of the vessel system 12 or the surrounding anatomy. Registration for such a three-dimensional data set may take place in any event, for example, if the three-dimensional data set was recorded with the same x-ray apparatus as the x-ray images. Registration, however, may be undertaken explicitly (e.g., gray-scale-based in that the mask images are used or landmark-based), as is basically known from the prior art. An embodiment also takes account, during registration, of center lines 28 that are known (e.g., at least in x-ray images) and may be brought into accord, for example, with center lines of vessels determined from the three-dimensional image data set.

Figure 9:
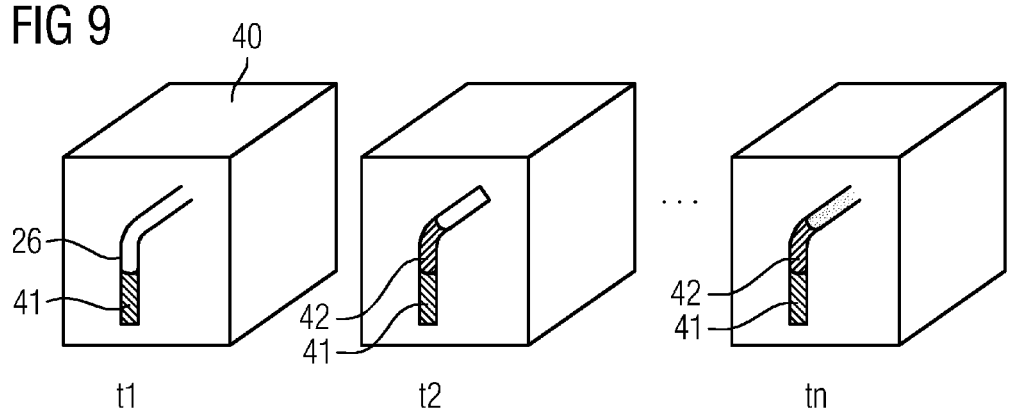
FIG. 9 shows the principle for representing a display data set.

A certain degree of four-dimensionality (e.g., a time component) may also be achieved, at least with regard to the representation, as described in detail below using the example of a display data set containing the TTP, making reference to FIG. 9. In FIG. 9, for the sake of simplicity, only one vessel 26 is shown in a representational volume 40 at different time points during the spreading of the contrast medium. The concept behind this type of representation is, in each case, only to reproduce, in a color-coded manner, the TTPs that have already been achieved so that an image of the spread of contrast medium through the vessel 26 is created. Thus, at time point t1, for example, two seconds after contrast medium administration, only one segment 41 is already contrast medium-filled. This may be discerned from the low TTP. At a time point t2, for example, three seconds after contrast medium administration, in addition to segment 41 that, for example, may be colored red, a further segment 42 is added that, for example, may be colored yellow. This is continued until, at a time point tn, the whole vessel 26 is displayed correspondingly color coded.

Figure 10:
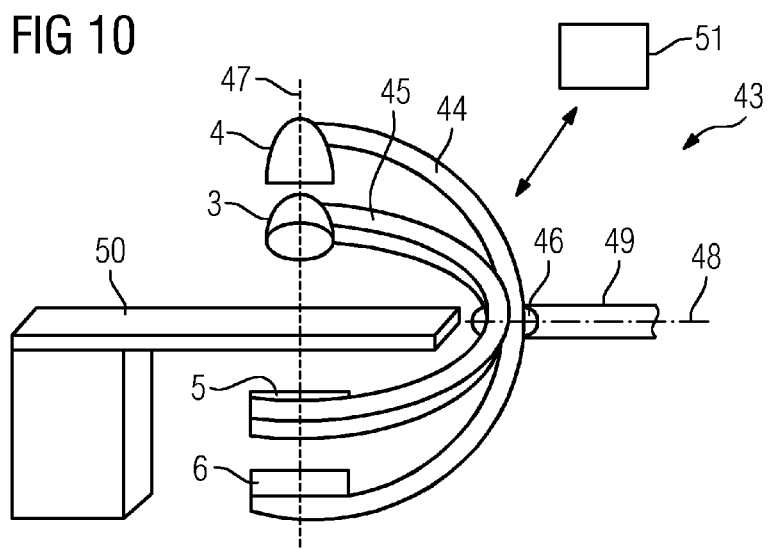
FIG. 10 shows one embodiment of an x-ray apparatus.

Finally, FIG. 10 shows an x-ray apparatus 43 according to one or more of the present embodiments. This is a biplane x-ray apparatus that includes two C-arms 44, 45 on which, in each case, an x-ray generator 3, 4 and an x-ray detector 5, 6 are arranged opposing one another, as shown. The C-arms 44, 45 are rotatable about a rotation axis 48 in a plane 47 using a pivot mounting 46. The C-arms 44, 45 are held by a mounting 49 that is merely suggested here. A patient support 50 is provided for positioning a patient.

Operation of the x-ray apparatus 43 is controlled by a control device 51 configured for carrying out the method according to one or more of the present embodiments and therefore on which, for example, a computer program according to one or more of the present embodiments is present.

Although the invention has been illustrated and described in detail based on the exemplary embodiments, the invention is not restricted by the examples given. Other variations may be derived therefrom by a person skilled in the art without departing from the protective scope of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating an at least three-dimensional display data set of a plurality of time parameters relating to chronological spreading of a contrast medium introduced into a vessel system from a series of chronologically successive x-ray images of digital subtraction angiography from at least two different projection directions showing the chronological spreading of the contrast medium, the method comprising:
determining a plurality of three-dimensional positions, each of the three-dimensional positions based on at least two correspondence points defined in different projection directions of digital subtraction angiography images, the at least two correspondence points for each different three-dimensional position marking the same vessel in the different projection directions of digital subtraction angiography images;
determining the plurality of time parameters, wherein each time parameter is determined for a different one of the plurality of three-dimensional positions, the determining of each of the plurality of time parameters comprising:
evaluating time-intensity curves for the at least two correspondence points to derive individual time parameters for different projection directions; and
combining the individual time parameters for different projection directions to derive one of the plurality time parameters for one of the plurality of three-dimensional positions;
displaying the at least three-dimensional display data set formed from the plurality of three-dimensional positions and the plurality of time parameters determined for each of the plurality of three-dimensional positions.

2. The method of claim 1, wherein the correspondence points are manually determined by a user.

3. The method of claim 1, wherein the correspondence points are determined from a vessel model based on center lines of vessels marked by a user.

4. The method of claim 3, wherein the vessel model is determined in three-dimensional space from mutually corresponding center lines in at least two projection directions.

5. The method of claim 3, wherein, by using the vessel model, registration takes place with a three-dimensional image data set of the vessel system.

6. The method of claim 1, wherein a registration takes place with a three-dimensional image data set of the vessel system taking account of at least one marker visible in the image data set, wherein, in at least one x-ray image, in a raw image underlying the x-ray image of a projection, gray-scale-based, or the projection and gray-scale-based, or in the at least one x-ray image and the raw image underlying the x-ray image of the projection direction, gray-scale-based, or the projection direction and gray-scale based, at least one raw image underlying an x-ray image of a projection direction is taken account of, the registration exists based on the use of an x-ray apparatus for recording the x-ray images that was also used for the recording of the three-dimensional image data set, or at least one raw image underlying an x-ray image of a projection direction is taken account of and the registration exists based on the use of an x-ray apparatus for recording the x-ray images that was also used for the recording of the three-dimensional image data set.

7. The method of claim 5, wherein the three-dimensional image data set is represented together with the at least three-dimensional display data set.

8. The method of claim 1, wherein, in order to determine three-dimensional positions, epipolar lines are assigned to the correspondence points.

9. The method of claim 1, wherein, in order to determine the three-dimensional position, the correspondence points in a plurality of different x-ray image sets recorded at different time points are taken into account.

10. The method of claim 1, wherein combining the individual time parameters for the different projection directions is carried out as an average formation.

11. The method of claim 1, wherein the combining the individual time parameters for the different projection directions is carried out as a weighted average formation.

12. The method of claim 10, wherein, in order to determine the individual time parameter for at least one projection direction, only one time-limited portion of the time-intensity curves is observed.

13. The method of claim 1, wherein, at a time point during the plurality of time parameters, a four-dimensional display data set is determined by displaying the time parameters only as the time point is reached.

14. The method of claim 1, wherein determining the plurality of time parameters comprises determining a time to a highest contrast medium concentration, a mean transit time, a relative cerebral blood volume, a relative cerebral blood flow, or any combination thereof.

15. An x-ray apparatus for generating an at least three-dimensional display data set of a plurality of time parameters relating to chronological spreading of a contrast medium introduced into a vessel system from a series of chronologically successive x-ray images of digital subtraction angiography from at least two different projection directions showing the chronological spreading of the contrast medium, the x-ray apparatus comprising:
a processor configured to:
determine a plurality of three-dimensional positions, each of the three-dimensional positions for at least two correspondence regions defined in different projection directions;
determine the plurality of time parameters assigned to the plurality of three-dimensional positions, the determination of each of the plurality of time parameters comprising an evaluation of time-intensity curves for the different projection directions for the at least one correspondence region over the series; and
display the at least three-dimensional display data set formed from the three-dimensional positions with the assigned time parameters, the displaying comprising applying a color code for the time parameters.

16. The x-ray apparatus of claim 15, wherein for each three-dimensional position assigned to the at least two correspondence regions, time-intensity curves are averaged over each correspondence region,
wherein one time parameter for each correspondence region is determined as a mean value of time parameters derived from individual time-intensity curves of each correspondence region.

17. The x-ray apparatus of claim 15, wherein for each three-dimensional position assigned to the at least two correspondence regions, time-intensity curves are averaged over each correspondence region,
wherein time-intensity curves are averaged over each correspondence region and one time parameter for each correspondence region is determined from the averaged time-intensity curves.

18. The x-ray apparatus of claim 15, wherein the correspondence regions are circular or are defined by a plurality of circular regions.

19. The x-ray apparatus of claim 15, wherein, in the case of overlapping three-dimensional positions and for different correspondence regions in intersecting regions, weighted averaging is carried out for the representation.

20. In a non-transitory computer-readable storage medium that stores instructions executable by a computer device to generate an at least three-dimensional display data set of a plurality of time parameters relating to chronological spreading of a contrast medium introduced into a vessel system from a series of chronologically successive x-ray images of digital subtraction angiography from at least two different projection directions showing the chronological spreading of the contrast medium, the instructions comprising:
determining, for at least two correspondence points defined in different projection directions of digital subtraction angiography images and at least two correspondence region defined in different projection directions of digital subtraction angiography images, a plurality of three-dimensional positions;
determining, for each three-dimensional position, a time parameter assigned to the three-dimensional position, the determining of the time parameter comprising evaluating time-intensity curves for the at least two different projection directions assigned to the at least two correspondence points and the at least two correspondence regions over the series; and
displaying the at least three-dimensional display data set formed from the three-dimensional positions with the assigned time parameters, the displaying comprising a representation of the at least three-dimensional display data set overlaid with a three-dimensional image data set of the vessel system.

* * * * *